United States Patent [19]

Findeisen

[11] 4,220,765
[45] Sep. 2, 1980

[54] PROCESS FOR THE PREPARATION OF 4,6-DIHALOGENO-TRIAZINES

[75] Inventor: Kurt Findeisen, Odenthal, Fed. Rep. of Germany

[73] Assignee: Bayer Aktiengesellschaft, Leverkusn, Fed. Rep. of Germany

[21] Appl. No.: 965,379

[22] Filed: Nov. 30, 1978

[30] Foreign Application Priority Data

Dec. 17, 1977 [DE] Fed. Rep. of Germany ....... 2756438

[51] Int. Cl.² .................. C07D 251/20; C07D 257/08
[52] U.S. Cl. .................................... 544/179; 544/212; 544/217; 544/216; 544/218
[58] Field of Search ............... 544/212, 217, 179, 218, 544/216

[56] References Cited
U.S. PATENT DOCUMENTS 2,858,310  10/1958  Grundmann et al. ............... 544/211

Primary Examiner—John M. Ford
Attorney, Agent, or Firm—Sprung, Felfe, Horn, Lynch & Kramer

[57] ABSTRACT

A process for the preparation of a 4,6-dihalogeno-triazine of the formula

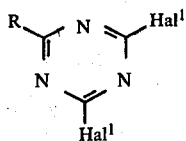

wherein
R represents an aryl or aryloxy radical or 5 or 6-membered nitrogen-containing aromatic heterocyclic radical which can be optionally mono or polysubstituted by a $C_1$–$C_4$-alkyl, $C_1$–$C_4$-alkoxy, halogeno, nitro, cyano, $C_1$–$C_4$-carbalkoxy, aryl or aryloxy and
$Hal^1$ denotes a halogen atom is described wherein a trihalogenomethyl compound of the formula $$R-C(Hal^2)_3$$

wherein
R has the meaning indicated above and
$Hal^2$ represents a halogen atom is reacted with $Hal^1$—CN in which $Hal^1$ has the meaning indicated above at a temperature of 50° to 200° C. in the presence of a Lewis acid. Optionally the process can be conducted in the presence of an inert solvent.

7 Claims, No Drawings

PROCESS FOR THE PREPARATION OF 4,6-DIHALOGENO-TRIAZINES

The invention relates to a process for the preparation of 4,6-dihalogeno-triazines substituted in the 2-position.

It is known to prepare 4,6-bis-alkylmercapto-1,3,5-triazines which are substituted in the 2-position from S,S'-dialkyl-dithiobiurets and acid chlorides and to convert these products into 4,6-dichloro-1,3,5-triazines which are substituted in the 2-position by subsequent reaction with elementary chlorine (Chem. Ber. 100, 1,874–1,891 (1967)).

A process has been found for the preparation of 4,6-dihalogeno-triazines of the formula

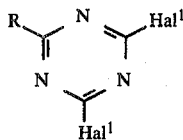
(I)

in which
R denotes an aryl or aryloxy radical or a 5-membered or 6-membered nitrogen-containing aromatic heterocyclic radical and can be optionally monosubstituted or polysubstituted by $C_1$–$C_4$-alkyl, $C_1$–$C_4$-alkoxy, halogen, nitro, cyano, $C_1$–$C_4$-carbalkoxy, aryl or aryloxy and
$Hal^1$ denotes a halogen atom,
which is characterised in that trihalogenomethyl compounds of the formula

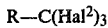 R—C(Hal²)₃    (II)

in which
R has the meaning indicated above and
$Hal^2$ represents a halogen atom, are reacted with a cyanogen halide of the formula

 Hal¹—CN    (III)

in which
$Hal^1$ has the meaning indicated above, at temperatures from about 50° to 200° C. in the presence of Lewis acids and optionally in the presence of an inert solvent. The halogen of $Hal^1$ can be the same or different halogen or that of $Hal^2$.

Aryl or aryloxy radicals (R) are derived from an aromatic carbocyclic system, for example from benzene, naphthalene or anthracene. Aryl or aryloxy radicals (R) which are derived from benzene are preferred. The phenyl and phenoxy radical are particularly preferred.

5-membered or 6-membered nitrogen-containing, aromatic, heterocyclic radicals are derived, for example, from pyrrole, pyrazole, imidazole, triazole, pyridine, pyrimidine, pyrazine, triazine and tetrazine.

The radicals R in the formula (I) and (II) can be monosubstituted or polysubstituted by $C_1$–$C_4$-alkyl, $C_1$–$C_4$-alkoxy, halogen, nitro, cyano, $C_1$–$C_4$-carbalkoxy, aryl or aryloxy e.g. phenyl and phenoxy.

An example of $C_1$–$C_4$-alkyl which may be mentioned is methyl, ethyl, propyl, isopropyl, butyl and isobutyl, preferably methyl and ethyl.

An example of $C_1$–$C_4$-alkoxy which may be mentioned is methoxy, ethoxy, propoxy, isopropoxy, butoxy or isobutoxy, preferably methoxy and ethoxy.

An example of halogen which may be mentioned is fluorine, chlorine, bromine and iodine, preferably chlorine and bromine.

Examples of $C_1$–$C_4$-carbalkoxy which may be mentioned are the methyl, ethyl, propyl, isopropyl, butyl or isobutyl esters of carboxylic acids, by which the radical R is substituted.

Examples of aryl or aryloxy which may be mentioned are those radicals which have already been mentioned for the definition of the radicals R themselves.

Examples of $Hal^1$ and $Hal^2$ which may be mentioned are halogen atoms, for example, fluorine, chlorine, bromine or iodine. Chlorine may be mentioned as the preferred halogen atom $Hal^1$ and $Hal^2$.

The following compounds may be mentioned as examples of trihalogenomethyl compounds of the formula (II) for the process according to the invention: benzotrichloride, o-, m- and p-chloro-benzotrichloride, dichloro-benzotrichlorides, o-, m- and p-methoxy-benzotrichloride, o-, m- and p-carbomethoxy-benzotrichloride, o-, m- and p-carboethoxy-benzotrichloride, o-, m- and p-methyl-benzotrichlorides, o- and p-phenyl-benzotrichloride, trichloro-methoxybenzene, o-, m- and p-chloro-(trichloro-methoxy)-benzene, dichloro-(trichloro-methoxy)-benzenes, o-, m- and p-nitro-(trichloro-methoxy)-benzenes, chloro-nitro-(trichloro-methoxy)-benzenes, o-, m- and p-cyano-(trichloro-methoxy)-benzenes, benzotribromide, o-, m- and p-bromo-benzotrichloride, o-, m- and p-bromo-benzotribromide, o-, m- and p-methoxy-(trichloro-methoxy)-benzene, o-, m- and p-carboethoxy-(trichloro-methoxy)-benzene, o-, m- and p-methyl-(trichloro-methoxy)-benzene, o- and p-phenyl-(trichloro-methyl)-benzene and o-, m- and p-methoxy-(tribromo-methyl)-benzene.

Examples of cyanogen halides of the formula (III) which may be mentioned are cyanogen fluoride, cyanogen chloride and cyanogen bromide. Cyanogen chloride is preferred for the process according to the invention.

The process according to the invention is carried out at temperatures from about 50° to about 200° C. The process is preferably carried out in the temperature range from about 100° to about 150° C.

The process according to the invention is carried out in the presence of Lewis acids. Possible Lewis acids are the Lewis acids which can be employed for Friedel-Crafts reaction are those set forth in Olah, Friedel-Crafts and Related Reactions, volume 1, page 201, Intersciens, 1963, the disclosure of which is specifically imparted herein by reference. Examples which may be mentioned are: iron-II, chloride, iron-III chloride, zinc chloride, tin-II-chloride, aluminium chloride, zinc cyanide and boron fluoride. Aluminium chloride and zinc chloride are preferably employed in the process according to the invention. It is particularly preferable to use aluminium chloride.

The Lewis acids are employed in an amount of 1 to 15 mol %, relative to the trihalogenomethyl compound of the formula (II) employed. It is preferable to use an amount of the Lewis acids of 3 to 8 mol %.

The process according to the invention can be carried out without solvents or in the presence of an inert solvent. Examples of inert solvents which may be mentioned are those which can also be employed for Friedel-Crafts reactions. Examples of preferred solvents which may be mentioned are: chlorobenzene, dichlorobenzenes, trichlorobenzenes and nitrobenzene.

One can, of course, use the reaction products of the process according to the invention as solvents.

The process according to the invention can be carried under normal pressure or under increased pressure. In the case of a procedure in a pressure vessel, for example in an autoclave, the process is preferably carried out under the autogenous pressure of the reactants which is set up spontaneously under the reaction conditions. Pressure up to 15 bar can be employed.

The molar ratio of trihalogenomethyl compounds of the formula (II) employed in the process according to the invention and the cyanogen halides of the formula (III) is in general 1:3 although the range of up to 1:6 is applicable. The use of less than 3 moles of cyanogen halide per mole of trihalogenomethyl compound is less advisable due to the incomplete course of reaction.

The process according to the invention can be illustrated by the equation which follows, with the aid of the reaction of benzotrichloride with canogen chloride to give 2-phenyl-4,6-dichloro-1,3,5-triazine:

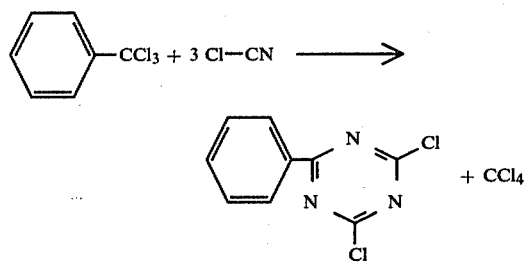

In general, the process according to the invention is carried out as follows: the trihalogenomethyl compound of the formula (II) and the Lewis acid are initially introduced and the mixture is warmed to the reaction temperature. The cyanogen halide of the formula (III) is then added dropwise, whilst maintaining the reaction temperature. The carbon tetrahalide formed is removed by distillation via a column and the product of the formula (I) according to the invention, which remains as the residue, is purified by customary working up, for example by recrystallization from ligroin.

The known substituted 4,6-dihalogeno-triazines are intermediate products for the preparation of dyestuffs and agents for combating pests.

Whilst the 4,6-dichloro-1,3,5-triazines substituted in the 2-position can be obtained according to the state of the art (Chem. Ber. 100, 1,874–1,891 (1967)) in a multistage synthesis, there is herein described a route to substituted 4,6-dihalogeno-1,3,5-triazines in one reaction step, using compounds which are readily commercially available.

The process according to the invention is to be regarded as exceptionally surprising, since it could be expected that the cyanogen halide of the formula (III) employed would undergo trimerization in the presence of Lewis acids to give cyanuric chloride, without involving the trihalogenomethyl compound of the formula (II) in the reaction.

EXAMPLE 1

140 g (0.5 mol) of 2,4-dichloro-trichloromethoxybenzene are warmed to 135° C. in the presence of 4 g of aluminum chloride, and 92.3 g (1.5 mols) of cyanogen chloride are added dropwise, whilst maintaining this temperature. After about 50 g of cyanogen chloride have been added, the addition is interrupted and the carbon tetrachloride formed is distilled off, and the rest of the cyanogen chloride is then added dropwise. The dark-colored reaction product is subjected to fractional distillation and the solid reaction products are recrystallized. Yield: 38 g of carbon tetrachloride (49% of the theoretical yield) and 70 g of 4,6-dichloro-2(2′, 4′-dichlorophenoxy)-1,3,5-triazine (45% of the theoretical yield). Melting point: 120°–122° C.

EXAMPLE 2

97.8 g (0.5 mol) of benzotrichloride are warmed to 100° C. in the presence of 2 g of aluminum chloride, and 92.2 g (1.5 mol) of cyanogen chloride are added dropwise in the course of 20 minutes. The heat liberated is removed by occasional cooling and the carbon tetrachloride formed is removed by distillation. After the dropwise addition has ended, the mixture is subsequently stirred at 130° C. for 30 minutes and then subjected to fractional distillation. Yield: 40 g of carbon tetrachloride (52% of the theoretical yield) and 69 g of 4,6-dichloro-2-phenyl-1,3,5-triazine (61% of the theoretical yield). Melting point: 119° C. (from wash benzine).

EXAMPLE 3

115 g (0.5 mol) of 4-chloro-benzotrichloride are warmed to 140° C. in the presence of 4 g of aluminum chloride and are reacted with 76 ml (1.5 mols) of cyanogen chloride in the course of 4 hours. After fractional distillation, 46 g of carbon tetrachloride ($\triangleq$65% of theory) and 91 g of 4,6-dichloro-2-(4′-chlorophenyl)-1,3,5-triazine (70% of the theoretical yield) are obtained. Melting point: 141°–143° C. (from wash benzine).

EXAMPLE 4

92.2 g (1.5 mols) of cyanogen chloride are added dropwise to 132 g (0.5 mol) of 2,4-dichloro-benzotrichloride in the presence of 5 g of aluminum chloride at 150° C. After the cyanogen chloride has been consumed, the low-boiling constituents are distilled off and the residue is recrystallized from wash benzine. Yield: 94 g of 4,6-dichloro-2-(2′,4′-dichloro-phenyl)-1,3,5-triazine (64% of the theoretical yield). Melting point: 118° C.

EXAMPLE 5

92.2 g (1.5 mols) of cyanogen chloride are added dropwise to 106 g (0.5 mol) of trichloro-methoxybenzene, after adding 3 g of zinc chloride, at 120° C. in the course of 2 hours. The carbon tetrachloride formed is distilled off; the residue is recrystallized from wash benzine. Yield: 69 g of 4,6-dichloro-2-phenoxy-1,3,5-triazine (57% of the theoretical yield). Melting point: 113°–114° C.

EXAMPLE 6

97.8 g (0.5 mol) of benzotrichloride, 2 g of aluminum chloride and 92.2 g (1.5 mols) of cyanogen chloride are introduced into an autoclave and the mixture is warmed to 120° C. for 2 hours. After the reaction has ended, the reaction product is subjected to fractional distillation; the high-boiling fraction is recrystallized. Yield: 77 g of 4,6-dichloro-2-phenyl-1,3,5-triazine (68% of the theoretical yield). Melting point: 119° C. (from wash benzine).

EXAMPLE 7

2 g of o-dichlorobenzene and 20 g of aluminum chloride are warmed to 140° C. in a reaction vessel and a mixture consisting of 1,150 g (5 mols) of 4-chlorobenzotrichloride and 922 g (1.5 mols) of cyanogen chloride are pumped in over a period of 2 hours in a manner such that the cyanogen chloride always reacts immediately; the carbon tetrachloride formed is distilled off via a column. Yield: 998 g of 2,4-dichloro-2-(4'-chlorophenyl)-1,3,5-triazine (76% of the theoretical yield). Melting point: 142°–143° C. (from wash benzine).

What is claimed is:

1. A process for the preparation of a 4,6-dihalogenotriazine of the formula

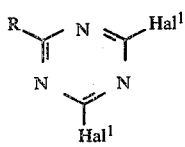

wherein

R represents phenyl or phenoxy radical or a 5 or 6-membered nitrogen-containing aromatic heterocyclic radical selected from the group consisting of pyrrolyl, pyrazoyl, imidazolyl, triazolyl, pyridinyl, pyrimidinyl, pyrazinyl, triazinyl and tetrazinyl which radicals can be optionally mono or polysubstituted by a $C_1$–$C_4$-alkyl, $C_1$–$C_4$-alkoxy, halogeno, nitro, cyano, $C_1$–$C_4$-carbalkoxy, phenyl or phenoxy and $Hal^1$ represents a halogen atom;

which comprises contacting a trihalogenomethyl compound of the formula $$R-C(Hal^2)_3$$

wherein

R has the meaning indicated above and $Hal^2$ represents a halogen atom, with $Hal^1$—CN wherein $Hal^1$ has the meaning indicated above at a temperature from about 50° to about 200° C. in the presence of a Lewis acid.

2. A process according to claim 1 wherein reactions conducted in the absence of a solvent.

3. A process according to claim 1 wherein the reaction is conducted in the presence of an inert solvent.

4. A process according to claim 1 wherein $Hal^1$ is the same halogen as $Hal^2$.

5. A process according to claim 1 wherein $Hal^1$ is a different halogen from that of $Hal^2$.

6. A process according to claim 1 wherein the compound $R-C(Hal^2)_3$ is a trichloromethyl compound and the same is reacted with a cyanogen chloride.

7. A process according to claim 1 wherein the reaction is conducted at a temperature from about 100° to 150° C.

* * * * *